United States Patent [19]
Matthews

[11] 3,965,737
[45] June 29, 1976

[54] METHOD AND APPARATUS FOR INDICATING THE AMOUNT OF TORQUE IN A YARN

[76] Inventor: Hubert B. Matthews, 301 Lindsay Ave., Greenwood, S.C. 29646

[22] Filed: Feb. 13, 1975

[21] Appl. No.: 549,675

[52] U.S. Cl. ................................. 73/160; 73/95.5
[51] Int. Cl.² .......................................... G01L 5/06
[58] Field of Search .................. 73/160, 95.5, 99

[56] References Cited
UNITED STATES PATENTS
2,154,631   4/1939   McNally ............................. 73/160

*Primary Examiner*—Donald O. Woodiel
*Attorney, Agent, or Firm*—Bailey & Dority

[57] ABSTRACT

A method and device for indicating the amount of torque in a yarn is disclosed wherein an elongated horizontal bar assembly has supported thereon a movable cantilevered arm member and a stationary cantilevered arm member having yarn clamps for receiving and clamping the yarn thereto whereby the movable arm member is moved towards said stationary arm member and the point at which the yarn held therebetween twists together into a loop is noted to indicate the torque therein.

10 Claims, 3 Drawing Figures

U.S. Patent   June 29, 1976   3,965,737
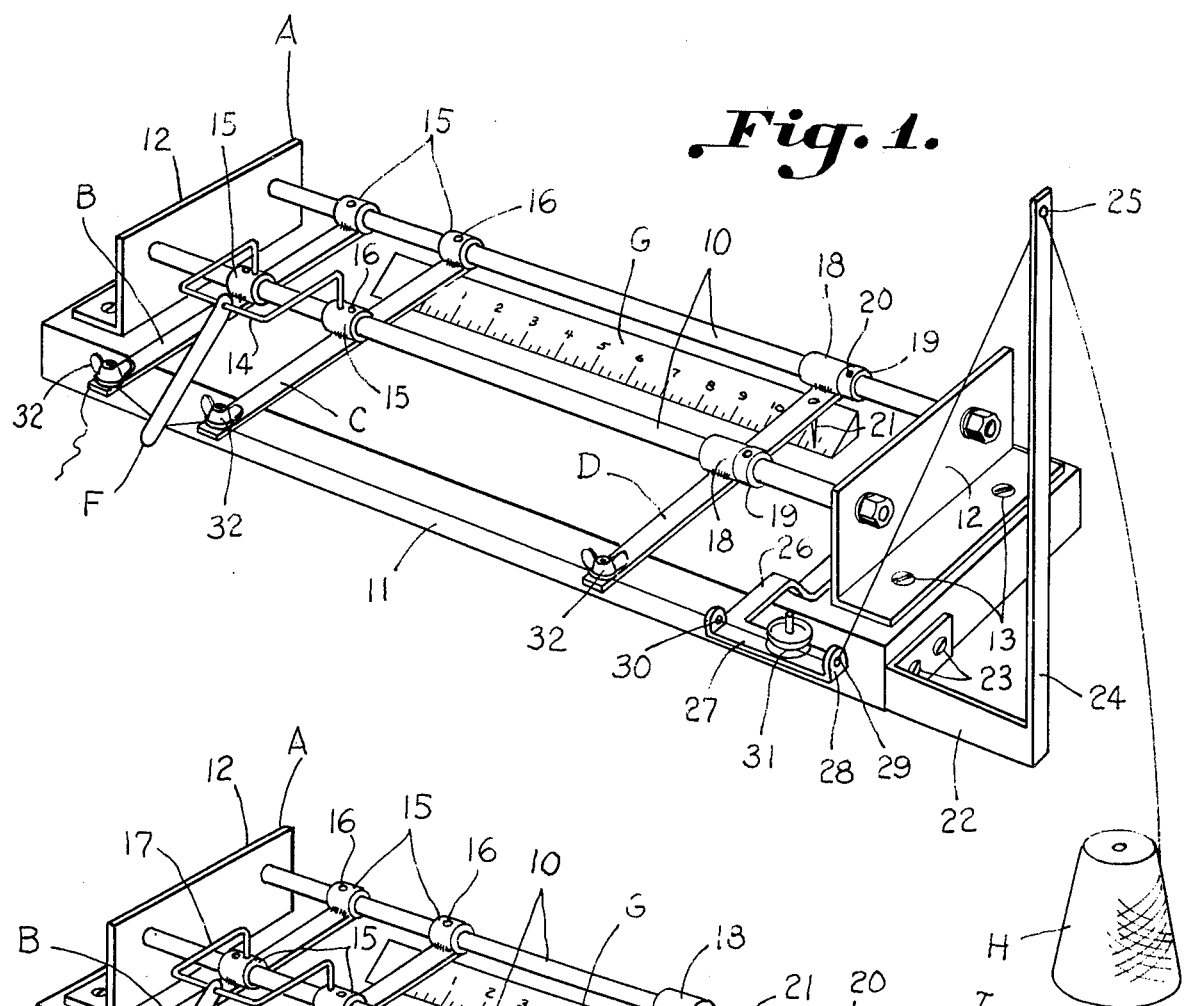
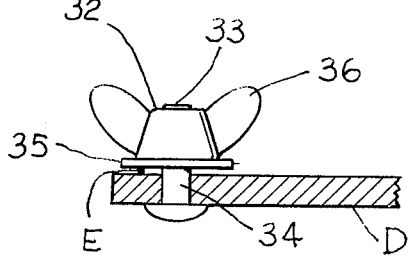 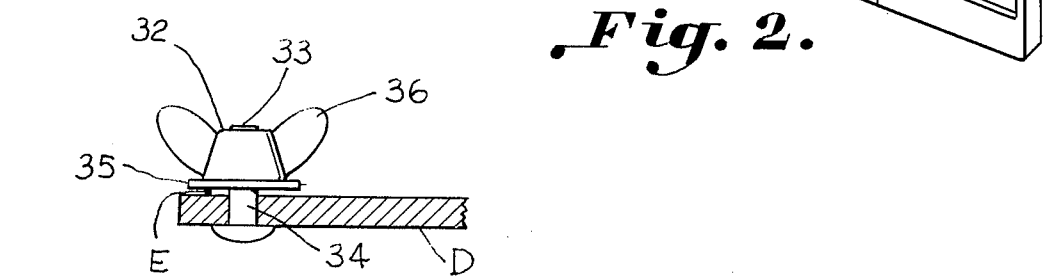

METHOD AND APPARATUS FOR INDICATING THE AMOUNT OF TORQUE IN A YARN

BACKGROUND OF THE INVENTION

Heretofore, efforts have been made to provide useful devices for determining characteristics of textile yarns such as strength, regularity, weight, and twist or torque. It is important to be able to accurately determine and know these characteristics so that the quality and appearance of the final cloth or fabric can be controlled. In particular, yarns with too much torque or twist cause problems in final woven and knit fabrics and such excessive torque may, in the case of spun yarns, be reduced by steaming the yarn. When we have problems with spun yarns, we have a tendency to overreact. Therefore, the amount of steam used to overcome a torque problem could possibly be reduced if the yarn torque is predetermined to be within the acceptable torque range. The individual customer could specify the required torque level for the product produced.

A textured yarn torque problem may be dealt with by varying the twist level as well as the heater temperature. Depending on whether the product is a stretch or set yarn, the condition will vary.

If, for example, a standardized test and index for the torque were available to both the yarn supplier and the knitting plant then the exact torque index for the yarn could be specified by the knitter and the supplier could predetermine that the yarn so supplied meets the specified torque index. The index, most likely, will vary by type machine and/or creel for the knitting machine as well as the conditioning in the plant.

A device for measuring variations in the elongation of a running length of yarn is described in U.S. Pat. No. 3,018,659 wherein a strain gauge mechanism is used to obtain a stress-strain curve on a running strand of yarn subjected to a predetermined load.

A prior device developed for measuring torque in yarn is described in U.S. Pat. No. 2,154,631 wherein a length of yarn is supported at two ends, one end being free to rotate. The yarn is immersed in a liquid which releases the torque in the yarn rotating the free end an amount proportional to the torque which is registered on an indicating drum. Such a device comprises a rather large number of intricate components which detracts from the accuracy and uniformity of the measurements made therefrom.

Accordingly, the main object of this invention is to provide a device which will indicate the torque in a textured or spun yarn in a reliable and uniform manner affording a uniform means of measuring the torque in a given yarn in a reliable manner.

Another important object of the present invention is to provide a device for indicating the amount of torque in a textured or spun yarn which is simple in construction and operation.

Another important object of the present invention is to provide a torque indicating device for predetermining torque in textured and spun yarns so that problem yarns can be eliminated prior to further processing, eliminating the need and expense of faulty fabric.

Another important object of the present invention is to provide a torque indicating device which is readily available for all types of textile manufacturing operations.

SUMMARY OF THE INVENTION

It has been found that torque in a yarn may be indicated by utilizing a pair of properly spaced yarn clamping supports mounted on an elongated bar assembly. The yarn clamping supports include first and second fixed spaced cantilevered arms carrying clamps for receiving and clamping the yarn to the ends thereof. An appropriate pretension means may be applied to the yarn manually, mechanically or automatically for tensioning the yarn held between the second cantilevered arm and the movable cantilevered yarn clamping support. When a movable support is moved towards the second cantilevered arm member the yarn held therebetween twists together into a loop and the point at which the loop occurs may be used to indicate the amount of torque therein.

The invention contemplates a stationary pair of fixed properly spaced yarn clamping supports and one movable clamping support which are all mounted on one or more elongated shafts.

BRIEF DESCRIPTION OF THE DRAWING

The construction designed to carry out the invention will be hereinafter described, together with other features thereof.

The invention will be more readily understood from a reading of the following specification and by reference to the accompanying drawing forming a part thereof, wherein an example of the invention is shown and wherein:

FIG. 1 is a perspective view illustrating a torque indicating device constructed in accordance with the present invention for carrying out the method of the present invention, FIG. 2 is a perspective view with parts omitted further illustrating the device for indicating torque in a yarn in accordance with the present invention with the yarn twisted, and FIG. 3 is an enlarged sectional elevation taken on the line 3—3 of FIG. 2 illustrating a yarn clamp for a torque indicating device constructed in accordance with the present invention.

DESCRIPTION OF THE PREFERRED EMBODIMENT

The drawing illustrates a device for indicating the amount of torque in a yarn including an elongated bar assembly A carrying stationary cantilevered arm members B and C and a movable cantilevered arm member D for supporting and clamping the yarn E at extremities thereof. Carried between arm members B and C is a tensioning means provided by a weighted bar F for applying a weight bias against the yarn held therebetween providing a predetermined tension in the yarn held between arm members C and D. An indexed scale G is provided below the movable arm member D whereby, when the arm member D is moved towards the stationary arm member C, the yarn held therebetween twists into a loop so that the point at which the loop occurs can be read on the index scale to indicate the torque in the yarn.

The torque indicating device is best illustrated in detail in FIG. 1. The elongated bar assembly A may include two bar members 10 supported on a platform 11 by a pair of transverse elongated L-shaped brackets 12. The brackets 12 are secured to the platform by suitable attachment means, such as screws 13 and the bar members 10 are attached to the brackets by inserting threaded portions 10a through holes formed in the vertical leg of bracket member 12 and securing the bars thereto by suitable fastening means such as nuts 14. The bracket 12 and bar members 10 at the opposite end of the platform are attached in the same manner.

The cantilevered arm members B and C are carried on the bar assembly A by sleeves 15 which slide on the bar member 10. Sleeves 15 are provided with set screws 16 which lock the arm members B and C in a stationary position on the bar assembly A. A bracket member 17 joins the cantilevered arm members B and C together and fixes the spaced distance therebetween.

The bracket 17 is fixed to the arm members B and C as by welding. The weighted bar F is carried pivotably by the bracket 17 for applying a weight bias against the yarn E held between the arm members B and C. The weight of the bar F is correlated to the denier of the filament or yarn being tested and preferably may have a weight of 0.05 gram per denier of the yarn.

The movable cantilevered arm member D is slideably carried on the bar members 10 by sleeves 18 which abut the fixed sleeves 19 which limit the travel of the movable arm D and provide an initial position for the movable arm. Set screws 20 are provided in the fixed sleeves 19 for locking the sleeves in position. The movable cantilevered arm member D carries a suitable indicator 21 for pointing to the appropriate indicia located on indexed scale G which is positioned and mounted on the platform 11 beneath the path of travel of the indicator 21. The indexed scale G is preferably a ruler device which is indexed with both a Metric and English system. The movable cantilevered arm member D may be moved manually along the bar assembly A or may be motorized so as to provide for a constant rate of travel along the bar assembly. The index character on scale G beneath the point of the indicator 21 may be read visually or alternately other means may be used such as an electronic eye or other precision instrumentation may be used.

To provide for uniform testing of the yarn E on the torque testing device, suitable yarn guiding means are provided including a horizontal bracket member 22 attached to the platform 11 by any suitable means, such as screws 23. A standard 24 extends vertically from the bracket 22. At an upper portion of 24 is an eye 25 for receiving yarn therethrough. A second bracket is provided having a leg 26 extending outwardly from the platform 11, mounted thereon in any suitable manner, and a leg 27 perpendicular to the leg 26 and parallel to platform 11. Extending upwardly from the leg 27 is a projection 28 carrying an eye 29 formed therein for receiving the yarn. At the other end of the leg 27 is a suitable eye 30 for guiding the yarn. Intermediate the eye 29 and the eye 30 is tensioning device 31 which includes a pair of opposed discs between which the yarn is tensioned. The guiding means thus described simulates tension in the yarn as would be applied by a knitting machine and the like, providing uniformity and accuracy in the testing procedure.

An example of a suitable yarn clamp 32, which may be used with the torque indicating device in accordance with the present invention, is shown carried adjacent the ends of cantilevered arm members B, C, and D and is best illustrated in FIG. 3. A threaded bolt 33 is inserted through a hole 34 formed at the end as is shown, for example, in movable cantilevered arm member D. Received over the threaded end of bolt 33 is a washer 35 and a suitable fastening means, such as wing-nut 36. It is important that the yarn E be clamped beneath the washer 35 so that when the wing-nut 36 is tightened down to clamp the yarn the yarn will not twist about the bolt 33. If the yarn were allowed to be clamped between the washer 35 and the wing-nut 36 the yarn might possibly twist about the bolt 33 resulting in too much tension being placed in the yarn.

OPERATION

A procedure for testing a specimen of yarn contemplates using a length of yarn pulled from the package of spool H. The yarn is placed beneath the clamps 32 on the arm members B, C, and D. The free end of the yarn should extend well past the arm member B. The clamp 32 on the arm member D should be tightened with the yarn beneath it and then the yarn is clamped in the same manner on arm member B. The weighted bar F is then brought to rest against the yarn causing the yarn to be drawn tightly over the arm member C. Then the clamp 32 is tightened securing the yarn to arm member C. In this manner a predetermined amount of tension is placed in the yarn held between arm members C and D. With the movable arm member D having been first set at the initial position (uppermost right position) on scale G, the movable arm member D is moved towards the stationary arm member C. Moving the arm member D towards stationary arm member C will allow the yarn held therebetween to twist together into a loop or kink 38 at some point along the scale G, as best seen in FIG. 2, as a result of the torque therein. At this point movement of the movable arm member D is discontinued and the appropriate index character on scale G, directly beneath the indicator arm 21, is read as being an indication of the amount of torque in the yarn. The higher the amount of torque, the sooner the loop 38 will occur as the arm member D is moved towards arm member C. Since the scale is numbered from left to right, a higher number will therefore indicate a greater amount of torque.

Thus, it can be seen that the torque testing device illustrated in accordance with the present invention is both a simple and reliable device for indicating the amount of torque in a yarn. The manner of testing a specimen of yarn under a predetermined uniform tension provides for a standard testing of a specimen of yarn which can be used for creating standard specifications for torque in yarn throughout the textile industry. By so doing, it can be seen that torque specifications can be given by the knitter to the yarn supplier having a torque testing device as illustrated herein who can then predetermine the torque of the yarn so supplied to insure that it meets the requested torque specifications. The torque of the yarn made at the mill may be predetermined and the corresponding torque index character may be placed on the packaged yarn. By creating torque standards for the textile industry the problems of having yarns of different or incompatible torques mixed together in the weaving or knitting process can be eliminated, as well as the lengthy process of finishing problem yarns with unnecessary amounts of steam.

While the device illustrated herein in accordance with the present invention, has been described as measuring the amount of torque in a yarn, it is also possible that the device may be used to measure the stiffness or strength of yarns.

What is claimed is:

1. A device for indicating torque in a yarn comprising:
   a. a support platform;
   b. an elongated member mounted on said support platform;
   c. a first member carried by said elongated member having means for receiving and clamping said yarn;
   d. a second member movably carried on said elongated member having means for receiving and clamping said yarn;
   e. tensioning means for applying a predetermined amount of tension to said yarn held between said first and second members;
   f. said second member being movable towards said first member causing said yarn to twist together into a loop; and
   g. means for indicating the point at which said loop occurs to indicate the amount of torque therein.

2. The structure set forth in claim 1 wherein said first and second members comprise first and second cantilevered arm members.

3. The structure set forth in claim 2 including:
   a. said indicator means carried by said second cantilevered arm member; and
   b. an indexed scale mounted on said support platform adjacent said indicator means providing a reading indicative of the torque in the yarn.

4. The structure set forth in claim 2 wherein said first cantilevered arm member includes a pair of laterally spaced cantilevered arms each having means for receiving and clamping said yarn adjacent one end thereof.

5. The structure set forth in claim 4 wherein said tensioning means includes a lever bar pivotably carried by said first cantilevered arm member providing a predetermined weight bias against said yarn held between said pair of cantilever arms.

6. A device for indicating torque in a yarn comprising:
   a. a support platform;
   b. a horizontal bar assembly mounted longitudinally on said support platform;
   c. a first cantilevered arm member carried by said bar assembly having means for receiving and clamping said yarn adjacent one end thereof;
   d. a second cantilevered arm member movably carried on said bar assembly having means for receiving and clamping said yarn adjacent one end thereof;
   e. tensioning means for applying a predetermined amount of tension to said yarn held between said first and second cantilevered arm members;
   f. indicator means carried by said second cantilevered arm member; and
   g. an indexed scale carried by said support platform adjacent said indicator means providing a reading indicative of the torque in the yarn;
   whereby said second cantilevered arm member is moved towards said first cantilevered arm member causing the length of yarn held therebetween to twist together into a loop at which point the index of said scale is read to indicate the torque in the yarn.

7. A device for measuring torque in yarn comprising:
   a. a pair of spaced yarn engaging supports;
   b. means for placing a predetermined tension in a sample length of yarn held between said supports;
   c. means mounting one of said supports for movement toward and away from the other of said supports until the tensioned yarn twists together; and
   d. means indicating the relative proximity of said supports when the yarn initially twists together;
   whereby a measure of the torque in the sample length of yarn may be had in terms of the relative proximity of said supports when the yarn initially twists together.

8. The method of determining the amount of torque in yarn comprising:
   a. securing a length of the yarn at a first point along its length to a movable support;
   b. securing the yarn at a second point along its length to a first stationary support;
   c. loosely supporting the yarn at a third point intermediate said first and second points across a second stationary support;
   d. applying a predetermined tension force to said yarn at a point intermediate said second and third points;
   e. clamping said yarn at said third point to said second stationary support;
   f. moving said movable support towards said second stationary support causing the yarn held therebetween to twist into a loop; and
   g. determining the amount of torque by noting the point at which said loop occurs.

9. The method of determining the amount of torque in a yarn comprising:
   a. securing a length of yarn at a first point along its length to a movable support;
   b. loosely supporting the yarn at a second point along its length across a stationary support;
   c. applying a predetermined amount of tension to said yarn;
   d. clamping the yarn at said second point fixedly to said stationary support;
   e. moving said movable support towards said stationary support causing said yarn held therebetween to twist into a loop; and
   f. determining the amount of torque by noting the point at which said loop occurs.

10. The method of determining the amount of torque in a yarn comprising:
    a. tensioning a length of said yarn between a movable clamping support and stationary clamping support;
    b. moving said movable support towards said stationary support causing said yarn tensioned therebetween to twist into a loop; and
    c. determining the amount of torque by indicating the point at which said loop occurs.

* * * * *